US012558348B2

(12) United States Patent  
Nash

(10) Patent No.: US 12,558,348 B2  
(45) Date of Patent: Feb. 24, 2026

(54) BIOACTIVE PHYTOCHEMICALS

(71) Applicant: Phytoquest Limited, Aberystwyth (GB)

(72) Inventor: Robert James Nash, Ystrad-Meurig (GB)

(73) Assignee: Phytoquest Limited, Aberystwyth (GB)

( * ) Notice: Subject to any disclaimer, the term of this patent is extended or adjusted under 35 U.S.C. 154(b) by 953 days.

(21) Appl. No.: 17/584,744

(22) Filed: Jan. 26, 2022

(65) Prior Publication Data

US 2022/0288049 A1 Sep. 15, 2022

Related U.S. Application Data

(63) Continuation of application No. PCT/GB2019/052098, filed on Jul. 26, 2019.

(51) Int. Cl.

| | |
|---|---|
| A61K 31/45 | (2006.01) |
| A23L 33/105 | (2016.01) |
| A61K 8/49 | (2006.01) |
| A61K 8/9789 | (2017.01) |
| A61K 36/42 | (2006.01) |
| A61P 29/00 | (2006.01) |
| A61Q 19/00 | (2006.01) |
| G01N 33/68 | (2006.01) |

(52) U.S. Cl.  
CPC ............ *A61K 31/45* (2013.01); *A23L 33/105* (2016.08); *A61K 8/4926* (2013.01); *A61K 8/9789* (2017.08); *A61K 36/42* (2013.01); *A61P 29/00* (2018.01); *A61Q 19/00* (2013.01); *G01N 33/6863* (2013.01); *A23V 2002/00* (2013.01); *A61K 2236/39* (2013.01)

(58) Field of Classification Search  
CPC .... A61K 31/45; A61K 8/9789; A61K 8/4926; A61K 36/42; A61K 2236/39; A23L 33/105; A61P 29/00; A61Q 19/00; G01N 33/6863; A23V 2002/00  
See application file for complete search history.

(56) References Cited

U.S. PATENT DOCUMENTS

| | | | |
|---|---|---|---|
| 6,927,294 B1 | 8/2005 | Petasis et al. | |
| 9,326,977 B2 | 5/2016 | Nash | |
| 2014/0309258 A1* | 10/2014 | Nash | C07D 211/60 514/315 |
| 2017/0035825 A1 | 2/2017 | Nash | |

FOREIGN PATENT DOCUMENTS

| | | |
|---|---|---|
| DE | 36 28 486 A1 | 2/1988 |
| JP | 2012-116764 A | 6/2012 |
| WO | WO 2009/103953 A1 | 8/2009 |
| WO | WO 2010/029313 A1 | 3/2010 |
| WO | WO 2013/054070 A1 | 4/2013 |

OTHER PUBLICATIONS

Olajide OA, Iwuanyanwu VU, Banjo OW, Kato A, Penkova YB, Fleet GWJ, Nash RJ. Iminosugar Amino Acid idoBR1 Reduces Inflammatory Responses in Microglia. Molecules. May 23, 2022;27(10):3342. (Year: 2022).*

Yoshimura, Yuichi, et al. "Synthesis of both enantiomers of hydroxypipecolic acid derivatives equivalent to 5-azapyranuronic acids and evaluation of their inhibitory activities against glycosidases." Bioorganic & medicinal chemistry 16.17 (2008): 8273-8286. (Year: 2008).*

Islam et al.,, Novel anti-adherence activity of mulberry leaves: inhibition of *Streptococcus* mutans biofilm by 1-deoxynojirimycin isolated from Morus alba, Journal of Antimicrobial Chemotherapy, vol. 62, Issue 4, Oct. 2008, pp. 75 (Year: 2008).*

Sudhakara et al., "Bacterial sialoglycosidases in virulence and pathogenesis." Pathogens 8.1 (2019): 39. (Year: 2019).*

Kuboniwa et al., "Subgingival biofilm formation." Periodontology 2000 52.1 (2010): 38 (Year: 2010).*

Chi, Y. et al. (2022) "Natural products from traditional medicine as promising agents targeting at different stages of oral biofilm development." Front. Microbiol. 13:955459 doi: 10.3389/fmicb.2022.955459 (Year: 2022).*

International Search Report and Written Opinion mailed Feb. 18, 2013 for Application No. PCT/GB2012/000768.

International Preliminary Report on Patentability mailed Apr. 24, 2014 in connection with PCT/GB2012/000768.

Bashyal et al., Enantiospecific Syntheses of 2S,3R,4R,5S-Trihydroxypipecolic Acid, 2R,3R,4R,5S-Trihydroxypipecolic Acid, 2S,4S,5S-Dihydroxypipecolic Acid, and Bulgecinine from D-Glucuronolactone. Tetrahedron Lett. 1986;27(27):3205-8.

Englebienne, Effects of introducing silicon isosteres in COX-2 inhibitors: a preliminary in silico evaluation. Med Chem. May 2005;1(3):215-26. doi: 10.2174/1573406053765459.

Kushner et al., Pharmacological uses and perspectives of heavy water and deuterated compounds. Can J Physiol Pharmacol. Feb. 1999;77(2):79-88.

Nash et al., Endometrial explant culture for characterizing equine endometritis. Am J Reprod Immunol. Feb. 2008;59(2):105-17. doi: 10.1111/j.1600-0897.2007.00548.x.

Tacke et al., Sila-substitution—a useful strategy for drug design? Endeavour. 1986;10(4):191-7.1986;10(4):191-7. doi: 10.1016/0160-9327(86)90093-1.

(Continued)

*Primary Examiner* — James H Alstrum-Acevedo  
*Assistant Examiner* — Justin Christopher Sanchez  
(74) *Attorney, Agent, or Firm* — Wolf, Greenfield & Sacks, P.C.

(57) ABSTRACT

Described are processes for the production of a composition comprising (2R, 3R, 4R, 5S)-3, 4, 5-trihydroxypiperidine-2-carboxylic acid (idoBR1), said process comprising the steps of: a) providing plant material from a botanical source comprising plant of the family Cucurbitaceae; b) fractionating said plant material to produce an extract enriched in idoBR1 c) assaying said extract for: i) inhibitory activity against sialidase or TNF-alpha or ii) IL-10 stimulatory activity; and d) formulating said assayed extract with a cosmetically-, nutraceutically- or pharmaceutically-acceptable excipient or carrier to produce a cosmetic, nutraceutical or pharmaceutical composition.

11 Claims, No Drawings

(56)                    References Cited

OTHER PUBLICATIONS

Watson et al., Glycosidase-inhibiting pyrrolidine alkaloids from Hyacinthoide non-scripta. Phytochemistry. Sep. 1997;46(2):255-9.

Watson et al., Polyhydroxylated alkaloids—natural occurrence and therapeutic applications. Phytochemistry. Feb. 2001;56(3):265-95. doi: 10.1016/s0031-9422(00)00451-9.

Invitation to Pay Additional Fees for Application No. PCT/GB2019/052098, mailed Mar. 11, 2020.

International Search Report and Written Opinion for Application No. PCT/GB2019/052098, mailed Jun. 24, 2020.

International Preliminary Report on Patentability for Application No. PCT/GB2019/052098, mailed Feb. 10, 2022.

Bietrix et al., Inhibition of Glycosphingolipid Synthesis Induces a Profound Reduction of Plasma Cholesterol and Inhibits Atherosclerosis Development in APOE*3 Leiden and Low-Density Lipoprotein Receptor-/-Mice. -7. doi: 10.1161/ATVBAHA.109.201673. Epub Feb. 18, 2010.

Greimel et al., Iminosugars and relatives as antiviral and potential anti-infective agents. Curr Top Med Chem. 2003;3(5):513-23. doi: 10.2174/1568026033452456.

* cited by examiner

BIOACTIVE PHYTOCHEMICALS

RELATED APPLICATIONS

This application is a continuation of and claims the benefit under 35 U.S.C. §§ 120 and 365(c) of International Patent Application No. PCT/GB2019/052098, filed Jul. 26, 2019 and entitled "BIOACTIVE PHYTOCHEMICALS," the entire content of which is incorporated herein by reference.

FIELD OF THE INVENTION

The present invention relates to processes for the production of compositions comprising (2R,3R,4R,5S)-3,4,5-trihydroxypiperidine-2-carboxylic acid (idoBR1), together with various products, compounds, compositions, medical uses and methods based thereon and their use in the preparation of various compositions for use in medicine, including the treatment of inflammation, infection, skin disorders, in vivo inhibition of sialidase activity, and to processes for isolating and purifying said compositions from various plant sources.

The invention also relates to methods for monitoring the quality of a Cucurbitaceae extract (for example, a *Cucumis* extract), to processes for producing a Cucurbitaceae extract as well as to Cucurbitaceae extracts (and in particular *Cucumis* extracts) obtainable by such processes.

BACKGROUND OF THE INVENTION

The cucumber (*Cucumis sativus*) is a widely cultivated plant in the gourd family Cucurbitaceae, which includes squash. Cucumbers originated in India and have been cultivated for at least 3000 years in Western Asia, and probably introduced to other parts of Europe by the Romans. Records of cucumber cultivation appear in France in the 9th century, England in the 14th century, and in North America by the mid-16th century.

Cucumbers and cucumber extracts have long been recognized as having anti-inflammatory properties, and have been used topically for various types of skin problems, including swelling under the eyes and sunburn. Cucumber was very popular in the ancient civilizations of Egypt, Greece and Rome, where it was used not only as a food but also for its skin healing properties.

Iminosugar acids (ISAs) constitute a subclass of the more widely distributed class of phytochemicals known as iminosugars. Many known ISAs are phytochemicals, present as secondary metabolites in plant tissues (where they may play a role in defence). While iminosugars are widely distributed in plants (Watson, A. et al., 2001, Phytochemistry 56, 265), the iminosugar acids are much less widely distributed and more difficult to isolate and identify (Martinez, R., et al., 2019, Amino acids 51, 991).

The iminosugar acid idoBR1 occurs in older cucumber varieties but is absent in certain modern commercial varieties. It has been shown to be a major component of certain cucumber fruits, and is the only iminosugar acid in cucumber. It is a minor component in certain squashes and gourds. WO2013/054070 identifies idoBR1 as an important bioactive principle in anti-inflammatory herbal medicines based on *Cucumis* extracts.

Herbal Food Additives and Remedies

There is presently great interest in the use of herbal remedies and supplements and a growing acceptance from food manufacturers, healthcare companies and the medical profession that herbal products have value and can complement established formulations and treatments. Herbal food additives and supplements are now widely used.

However, quality control of herbal food additives is difficult due to the complex nature and inherent non-uniformity of plant materials. The materials used in herbal and plant-based food additives are usually whole plants or parts or extracts thereof. Since plant materials contain many different chemical components the materials are complex mixtures. This makes it very difficult to standardize and control the quality of the materials. Moreover, many herbal food additives are mixtures of two or more plant-based components and are therefore mixtures of mixtures, so introducing a further level of complexity. Furthermore, the recipes and methods of manufacture used are often not uniform and may remain undisclosed. These factors make it very difficult to ensure that two samples of a given product, obtained from disparate sources and ostensibly identical, do in fact contain the same mixture of ingredients. This problem, which leads to difficulties in controlling the quality of such materials, has limited the use of certain herbal extracts even amongst herbal practitioners.

Other problems arise from the fact that the plants used in the practice of herbal medicine or as food supplements/nutraceuticals are frequently unavailable locally and therefore need to be obtained from sources which are remote from the end user. However, the supply of such plants from remote locations can be erratic and inaccurate, particularly because no detailed monographs including identity and quality standards exist for many such plants.

The complex mixture of ingredients found in medicinal plants varies widely in type and concentration depending on many factors including the botanical source, the location where the plant is grown, what other plants or microorganisms are growing near it, the time of year when the plant is harvested, the conditions under which the material is stored and processed and the extraction procedure used.

There is therefore a need for sensitive processes which can profile herbal products containing idoBR1 and so establish a standard specification for a plant-derived product which can be related to activity, so permitting quality control in the production of herbal medicines, food additives, cosmetics, nutraceuticals and food additives and ideally quantifying (structurally and/or functionally) the bioactive principles.

The present inventor has now discovered that idoBR1 exhibits inhibitory activity against sialidase and TNF-alpha, while exhibiting IL-10 stimulatory activity. This finding permits the development of improved processes for formulating cosmetic, nutraceutical or pharmaceutical compositions based on extracts from plant material from a botanical source comprising plants of the the family Cucurbitaceae, since the relevant bioactive principle, idoBR1, can now be quickly and easily functionally assayed following fractionation of the plant material.

Thus, the provision of cosmetic, nutraceutical or pharmaceutical compositions conforming to a standard specification is greatly facilitated: the invention permits rapid assay of the functional quality of the extract. It also renders time-consuming and expensive physical characterization (e.g. by GC-MS and/or HPLC) optional. Moreover, since the functionality of the extract is assayed, the impact of possible interference/inhibition by co-extracted moieties can be monitored. This may be particularly important in the case of cosmetic applications where the extract is formulated for topical application.

SUMMARY OF THE INVENTION

Thus, according to the invention there is provided a process for the production of a composition comprising (2R,3R,4R,5S)-3,4,5-trihydroxypiperidine-2-carboxylic acid (idoBR1), said process comprising the steps of:

(a) providing plant material from a botanical source comprising plants of the the family Cucurbitaceae;

(b) fractionating said plant material to produce an extract enriched in idoBR1;

(c) assaying said extract for: (i) inhibitory activity against sialidase or TNF-alpha; or (ii) IL-10 stimulatory activity; and (d) formulating said assayed extract with a cosmetically-, nutraceutically- or pharmaceutically-acceptable excipient or carrier to produce a cosmetic, nutraceutical or pharmaceutical composition.

The botanical source may comprise plants of the genus *Cucumis* or *Cucurbita*. Preferred species of the genus *Cucumis* are plants of the species *Cucumis sativus* (cucumber). Preferred species of the genus *Cucurbita* are the species *Cucurbita melos* or *Cucurbita moschata*.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The phrase "consisting essentially of" is used herein to require the specified integer(s) or steps as well as those which do not materially affect the character or function of the claimed invention.

As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, pathological variegated states). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

The term "subject" (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals and pet animals. In preferred embodiments, the subject is a human.

References herein to the treatment of diabetes are to be interpreted to include the treatment of type 1 and type 2 diabetes per se as well as pre-diabetes (incipient diabetes) and insulin resistance. The term "pre-diabetes" or "incipient diabetes" defines conditions in which elevated levels of glucose or glycosylated haemoglobin are present in the absence of diabetes.

As used herein, an effective amount of a compound or composition defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

The term phytochemical is used herein in a broad sense to encompass any chemical constituent of a plant, including macromolecules and small molecules. Important examples include alkaloids (for example iminosugars and iminosugar acids, e.g. selected from the structural classes pyrrolidines, piperidines, pyrrolizidine, indolizidines, tropanes and nortropanes), carbohydrate analogues, phenolic compounds, terpenoids, enzyme inhibitors, glycosides, nucleotides, amino acids, lipids and sugars.

The term isolated as applied to the compounds of the invention is used herein to indicate that the compound exists in a physical milieu distinct from that in which it occurs in nature. For example, the isolated compound may be substantially isolated (for example enriched or purified) with respect to the complex cellular milieu in which it naturally occurs. The isolated compound may therefore take the form of an enriched fraction or extract of any of the botanical sources described herein.

When the isolated material is enriched or purified, the absolute level of enrichment or purity is not critical and those skilled in the art can readily determine appropriate levels according to the use to which the material is to be put. Preferred are purity levels of at least 0.1% w/w, 0.2% w/w, 0.3% w/w, 0.4% w/w, 0.5% w/w, 0.6% w/w, 0.7% w/w, 0.8% w/w, 0.9% w/w, 1.0% w/w, 1.1% w/w, 1.2% w/w, 1.3% w/w, 1.4% w/w, 1.5% w/w, 1.6% w/w, 1.7% w/w, 1.8% w/w, 1.9% w/w or 2.0% w/w.

Particularly preferred are purity levels of at least 0.5-2.0% w/w, for example at least 0.8-1.5% w/w, for example at least about 1.0% w/w. Levels of 5-10% w/w may be readily obtained in cases where the material is isolated from natural sources, if necessary, by employing suitable enrichment techniques, such as ion exchange chromatography.

In some circumstances, the isolated compound forms part of a composition (for example a more or less crude extract containing many other substances) or buffer system, which may for example contain other components. In other circumstances, the isolated compound may be purified to essential homogeneity, for example as determined spectrophotometrically, by NMR or by chromatography (for example GC-MS of the trimethylsilyl-derivatives).

The term herbal medicine is used herein to define a pharmaceutical composition in which at least one active principle (e.g. the compound) is not chemically synthesized and is a phytochemical constituent of a plant. In most cases, this non-synthetic active principle is not isolated (as defined herein), but present together with other phytochemicals with which it is associated in the source plant. In some cases, however, the plant-derived bioactive principle(s) may be in a concentrated fraction or isolated (sometimes involving high degrees of purification). In many cases, however, the herbal medicine comprises a more or less crude extract, infusion or fraction of a plant or even an unprocessed whole plant (or part thereof), though in such cases the plant (or plant part) is usually at least dried and/or milled. The herbal medicine may be in the form of a food supplement, food additive, nutraceutical, a beverage or presented in unitary doses as a herbal pharmaceutical kit or pack.

The term herbal food is used herein to define a composition in which at least one component is not chemically synthesized but rather is a phytochemical constituent of a plant. In most cases, this non-synthetic component is not purified, but present together with other phytochemicals with which it is associated in the source plant. In some cases, however, the plant-derived component(s) may be in a concentrated fraction or isolated (sometimes to high degrees of purity). In many cases, however, the herbal food additive comprises a more or less crude extract, infusion or fraction of a plant or even an unprocessed whole plant (or part thereof), though in such cases the plant (or plant part) is usually at least dried and/or milled. The term therefore includes herbal foods in the form of additives and supplements for use with foods and beverages.

The term bioactive principle is used herein to define a phytochemical which is necessary or sufficient for the pharmaceutical efficacy of the herbal medicament in which it is comprised. In the case of the present invention, the bioactive principle comprises idoBR1.

The term nutraceutical is used herein to define a food product (or isolate thereof) which provides physiological benefits or protects against disease. Preferred nutraceuticals of the invention are anti-inflammatory.

The term standard specification is used herein to define a characteristic, or a phytochemical profile, which is correlated with an acceptable quality of the herbal medicine, cosmetic or nutraceutical. In this context, the term quality is used to define the overall fitness of the product for its intended use, and includes the activity of ido BR1 at an appropriate concentration.

The term phytochemical profile is used herein to define a set of characteristics relating to different phytochemical constituents.

Functional Assays

The extracts of the invention are assayed for: (i) inhibitory activity against sialidase or TNF-alpha; or (ii) IL-10 stimulatory activity. The functional assay may comprise a biological assay. Biological assays may be carried out in vivo or in vitro, and may include enzyme inhibition assays (for example sialidase inhibition). Other biological assays include receptor binding assays, cellular assays (including cell replication, cell-pathogen and cell-cell interaction and cell secretion assays), immunoassays, anti-microbial activity (e.g. bacterial and viral cell-binding and/or replication) assays and toxicity assays (e.g. $LD_{50}$ assays).

Functional characterization may also be carried out indirectly by a form of characterization which permits the identification of one or more indices of biological activity.

Exemplary techniques are described in more detail below.

Sialidase

Inhibition of sialidase (neuraminidase) activity by idoBR1 or extracts containing it can be determined by an enzymatic assay in which neuraminidase activity is measured using, for example, enzyme from *Clostridium perfringens* (Sigma-Aldrich). The assay is based on the enzyme cleaving the 2'-(4-Methylumbelliferyl)-$\alpha$-D-N-acetyineuraminic acid (MUNANA) substrate to release the fluorescent product 4-methylumbelliferone (4-MU). Therefore, the inhibitory effect is determined based on the concentration of the idoBR1 or extract that is required to reduce 50% of the enzyme activity (to give an $IC_{50}$ value).

A suitable method may be as follows:
1. Prepare the reaction mixture. Sodium phosphate buffer (pH 4.5), 10 mmol MUNANA4MU-NeuAc (100 µl in buffer), 0.1 mg Enzyme in 100 µl, 100 µl plant extract or compound
2. Incubate for 10-30 min at 37 C.
3. Terminate the reaction by addition of 1.25 ml 0.25 M glycine-NaOH (pH 10.4).
4. Measure fluorometrically 4-methylumbelliferone (4-MU) released (emission 448 nm, excitation 365 nm).

TNF-$\alpha$ and IL-10

Decreased TNF-$\alpha$ and increased IL-10 by extracts can be measured either in cell cultures (e.g. THP-1 monocyte cells) or whole blood samples using ELISA methods.

THP-1 cells are commercially available. Cultured cells can be placed in RPMI complete medium in microtitre plates (e.g. 5 cells per well in 96 well plates) and after 24 hrs incubation, PMA (10 ng/mi) added to 96 well plate to differentiate THP-1 cells and to determine the effects on TNF-$\alpha$ and IL-10 production. The cells should be pretreated with cucumber extract at, for example, 200 µg/ml to 25 µg/ml followed by 2 hr LPS (100 ng/ml) stimulation. Post incubation, the cell supernatant is aspirated from each of the wells into sterile micro centrifuge tubes and centrifuged at 1000 rpm for 2-3 mins to settle any cells if present. The cell supernatant is then used for evaluation of presence of TNF-$\alpha$ or IL-10 using ELISA. Sandwich ELISA plates coated with suitable antibody are widely available (e.g. R&D Systems, USA).

For whole blood measurements, aliquots (800 µl) of whole blood can be incubated with the extract dissolved in RPMI 1640 for a 48 hr preincubation period after which LPS (10 µg/ml) is added and incubations continued for a further 20 hr at 37° C. in a humidified (100%) atmosphere of 5% $CO_2$ in air. At the end of the incubation period, supernatants consisting of plasma are collected by centrifugation at 10,000 g for 30 seconds at room temperature and TNF-α and IL-10 levels measured using human TNF-α and IL-10 ELISA assays (kits available for example from BioSource Europe S.A., Belgium).

Physical Characterization

The extracts of the invention may also be physically characterized (though this is not essential). This can take the form of quantification of the phytochemical component(s) present in any given fraction or at any other stage in the process, measurement of the purity of the constituents, determination of molecular weight (or molecular weight distribution or various statistical functions thereof in the case of fractions which comprise a plurality of different phytochemical constituents), determination of the molecular formula(e) (e.g. by nuclear magnetic resonance) and various spectral analyses.

Particularly useful spectral characteristics include:

Mass spectra (e.g. the mass to charge (m/z) value versus abundance), and/or

Chromatographic data (e.g. spectra, column retention times, elution profiles etc), and/or Photodiode array (PDA) spectra (e.g. in both UV and visible ranges), and/or electrochemical detection (ED) or evaporative light scattering (ELSD) detection; and/or Nuclear magnetic resonance (NMR) spectra (including spectral data sets obtained via $^1H$ and/or $^{13}C$ NMR).

Spectral characterization can be coupled with the fractionation step. For example, GC-MS and HPLC-PDA-MS-ED-ELSD can be used (as described herein) to couple the fractionation with the obtention of mass spectral, UV-visible spectral, electrochemical response or fraction mass data and chromatographic spectral data.

Any or all of the above characteristics can be used to define a "chemical fingerprint" for any given sample (or any fraction or phytochemical constituent thereof).

Chemical Characterization

The extracts of the invention can also be chemically characterized (though this is not essential). This can take the form of measurements inter alia of the chemical reactivity of phytochemical constituent(s), their solubility, stability and melting point.

Medical Uses of the Compounds of the Invention

Neoplasia

The compounds of the invention are sialidase inhibitors, and so find application in the treatment or prophylaxis of diseases and disorders mediated by sialidase activity and/or sialic acid.

Sialidases are involved in a variety of pathological processes, including bacterial and viral infections and neoplasia, which makes these enzymes an attractive therapeutic target. The expression of the sialidases Neu1 and Neu3 appear to be altered in diabetes (e.g. Neu1 activity discussed by Natori, Y., et al, 2013, Biol. Pharm., Bull., 36, 1027). Sialidases are also implicated in atherogenesis (Sukhorukov, V. N., et al., 2017, Curr. Pharm. Des., 23, 4696) and osteo-arthritis (Katoh, S., et al., 1999, J Immunol., 162, 5058).

The compounds of the invention therefore find application in the treatment or prophylaxis of neoplasia/proliferative disorders, as described in more detail below.

As used herein, the term "neoplasia" is used sensu stricto to define diseases involving the abnormal proliferation of neoplastic cells. The term includes benign, pre-cancerous and malignant neoplasia (as defined above) and is used synonymously with the term "proliferative disorder".

Neoplasia arises from inappropriately high levels of cell division and/or low levels of apoptosis or senescence in neoplastic cells which have acquired genetic or epigenetic changes which free them from normal physiological control (i.e. the cells have been "transfomed"). Neoplasia typically produces structures known as neoplasms: abnormal masses of tissue, the growth of which exceeds and is uncoordinated with that of the normal tissues and which persists in the same excessive manner after cessation of the stimulus which evoked the change. While most neoplasms form large masses of tissue (solid tumours), some neoplasms form no such discrete tissue mass. These include cervical intraepithelial neoplasias, anal intraepithelial neoplasias and leukemia.

Neoplasia may be benign, potentially malignant or malignant. Benign neoplasias include uterine fibroids and melanocytic naevi (skin moles) which are not invasive and which do not transfom or progress into malignant neoplasms. Potentially malignant (pre-cancerous) neoplasms include carcinoma in situ, which is not invasive but which in time transforms into a malignant neoplasm.

Malignant neoplasia gives rise to neoplasms (tumours) which invade and destroy the surrounding tissue, may form metastases and eventually kill the host. The terms "malignant neoplasia" and "cancer" are used as synonyms herein.

The terms "proliferative disorder" and "neoplasia" may be used herein as synonyms to define a class of diseases which involve the pathological growth of cells in vivo.

Proliferative disorders therefore include cancer, cancer metastasis, smooth muscle cell proliferation, systemic sclerosis, cirrhosis of the liver, adult respiratory distress syndrome, idiopathic cardiomyopathy, lupus erythematosus, retinopathy (e.g. diabetic retinopathy), cardiac hyperplasia, benign prostatic hyperplasia, ovarian cysts, pulmonary fibrosis, endometriosis, fibromatosis, harmatomas, lymphangiomatosis, sarcoidosis and desmoid tumours. Neoplasia involving smooth muscle cell proliferation include hyperproliferation of cells in the vasculature (e.g. intimal smooth muscle cell hyperplasia, restenosis and vascular occlusion, including in particular stenosis following biologically- or mechanically-mediated vascular injury, such as angioplasty). Moreover, intimal smooth muscle cell hyperplasia can include hyperplasia in smooth muscle other than the vasculature (e.g. blockage of the bile duct, bronchial airways and in the kidneys of patients with renal interstitial fibrosis). Non-cancerous proliferative disorders also include hyperproliferation of cells in the skin such as psoriasis and its varied clinical forms, Reiter's syndrome, *pityriasis rubra pilaris* and hyperproliferative variants of disorders of keratinization (including actinic keratosis, senile keratosis and scleroderma).

The term "neoplasia" is also used herein sensu lato to define diseases involving the abnormal growth and/or differentiation of cells in vivo, so encompassing hyperplasia, metaplasia and dysplasia.

Hyperplasia defines conditions in which normal (untransformed) cells within an organ or tissue proliferate to an abnormal extent. It may therefore result in the gross enlargement of an organ, the formation of a benign tumour, or may be visible only under a microscope. Hyperplasia is a physiological response to a specific stimulus and the hyperplastic cells remain subject to normal regulatory control mechanisms (unlike neoplastic growth, in which cells proliferate in an abnormal manner which is unresponsive to normal physiological control). Examples include congenital adrenal hyperplasia, endometrial hyperplasia, benign prostatic hyperplasia (prostate enlargement), hyperplasia of the breast (including ductal hyperplasia), focal epithelial hyperplasia (Heck's disease), sebaceous hyperplasia and liver hyperplasia.

Metaplasia defines conditions in which cells of one mature, differentiated type are replaced by cells of another mature, differentiated type. Examples include squamous metaplasia of the columnar epithelial cells of salivary gland ducts (when stones are present), squamous metaplasia of the transitional epithelium of the bladder (again, when stones are present or associated with infection), glandular metaplasia of the oesophagus in patients with gastric acid reflux (Barrett's esophagus) and osseous metaplasia in connective tissue.

Dysplasia defines conditions characterized by the abnormal maturation of cells within a tissue. This generally consists of an expansion of immature cells, with a corresponding decrease in the number and location of mature cells. For example, epithelial dysplasia of the cervix is characterized by an increased population of immature cells which are restricted to the mucosal surface. Myelodysplastic syndromes, or dysplasia of blood-forming cells, show increased numbers of immature cells in the bone marrow and a decrease in mature, functional cells in the blood. Other examples include neurofibromatosis.

Hyperplasia, metaplasia, and dysplasia are generally reversible conditions, being the result of a stimulus (e.g. insult or injury). In contrast, neoplasia is generally irreversible and associated with cellular transformation.

The compounds of the invention find general application in the treatment of any neoplasia, including proliferative disorders, benign, pre-cancerous and malignant neoplasia, hyperplasia, metaplasia and dysplasia.

The invention therefore finds application in the treatment of proliferative disorders which include, but are not limited to cancer, cancer metastasis, smooth muscle cell proliferation, systemic sclerosis, cirrhosis of the liver, adult respiratory distress syndrome, idiopathic cardiomyopathy, lupus erythematosus, retinopathy (e.g. diabetic retinopathy), cardiac hyperplasia, benign prostatic hyperplasia, ovarian cysts, pulmonary fibrosis, endometriosis, fibromatosis, harmatomas, lymphangiomatosis, sarcoidosis and desmoid tumours. Neoplasia involving smooth muscle cell proliferation include hyperproliferation of cells in the vasculature (e.g. intimal smooth muscle cell hyperplasia, restenosis and vascular occlusion, including in particular stenosis following biologically- or mechanically-mediated vascular injury, such as angioplasty). Moreover, intimal smooth muscle cell hyperplasia can include hyperplasia in smooth muscle other than the vasculature (e.g. blockage of the bile duct, bronchial airways and in the kidneys of patients with renal interstitial fibrosis). Non-cancerous proliferative disorders also include hyperproliferation of cells in the skin such as psoriasis and its varied clinical forms, Reiter's syndrome, Pityriasis rubra pilaris and hyperproliferative variants of disorders of keratinization (including actinic keratosis, senile keratosis and scleroderma).

Particularly preferred is the treatment of malignant neoplasia (cancer). The invention finds application in the treatment of any cancer, including those selected from the following major groupings: (a) carcinoma; (b) blastoma; (c) leukemia; (d) lymphoma; (e) myeloma; (f) sarcoma and (g) cancers of mixed type.

Carcinoma refers to a malignant neoplasm of epithelial origin or cancer of the internal or external lining of the body.

Carcinomas, malignancies of epithelial tissue, account for 80 to 90 percent of all cancer cases. Epithelial tissue is found throughout the body. It is present in the skin, as well as the covering and lining of organs and internal passageways, such as the gastrointestinal tract. In preferred embodiments the carcinoma treated according to the invention is selected from carcinomas of: salivary glands; colon; rectum; appendix; lung; thymus; breast; cervix uteri; bladder and eye.

The invention finds application in the treatment of all blastomas, including hepatoblastomas (e.g. nephroblastomas, nonepithelial renal tumours, rhabdoid renal tumour, kidney sarcomas and pPNET of the kidney), medulloblastomas, pancreatoblastomas, pulmonary blastoma, pleuropulmonary blastoma, neuroblastomas (including peripheral nervous cell tumours in general as well as ganglioneuroblastoma and retinoblastomas).

The invention finds application in the treatment of all leukemias, myeloproliferative diseases and myelodysplastic diseases, including: lymphoid leukemias (for example precursor cell leukemias, mature B-cell leukemias, mature T-cell leukemias and NK cell leukemias): acute myeloid leukemias: chronic myeloproliferative diseases; myelodysplastic syndrome and other myeloproliferative diseases. The invention therefore finds application in the treatment of various leukemias, including lymphatic, lymphocytic, or lymphoblastic leukemia (malignancy of the lymphoid and lymphocytic blood cell series) and polycythemia vera or erythremia (malignancy of various blood cell products, but with red cells predominating).

Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Unlike the leukemias which are sometimes called "liquid cancers." lymphomas are "solid cancers". Lymphomas may also occur in specific organs such as the stomach, breast or brain. These lymphomas are referred to as extranodal lymphomas. The lymphomas are subclassified into two categories: Hodgkin lymphoma and Non-Hodgkin lymphoma. The presence of Reed-Stenberg cells in Hodgkin lymphoma diagnostically distinguishes Hodgkin lymphoma from Non-Hodgkin lymphoma. The invention finds application in the treatment of all such lymphomas and reticuloendothelial neoplasms, including: (a) Hodgkin lymphomas; (b) Non-Hodgkin lymphomas (for example precursor cell lymphomas, mature B-cell lymphomas, mature T-cell lymphomas and NK-cell lymphomas; (c) Burkitt lymphoma and (d) other lymphoreticular neoplasms, including mantle cell lymphoma.

The invention therefore finds application in the treatment of a wide range of lymphomas, including for example tumours of the glands or nodes of the lymphatic system (including the spleen, tonsils, and thymus) and extranodal lymphomas of the stomach, breast and brain.

Myeloma is cancer that originates in the plasma cells of bone marrow. The invention therefore finds application in the treatment of hematopoieitic tumours and haematological malignancies, including those of lymphoid lineage (e.g. leukaemia, acute lymphocytic leukaemia, chronic lymphocytic leukaemia, B-cell lymphoma (such as diffuse large B cell lymphoma), T-cell lymphoma, Hodgkin's lymphoma, Non-Hodgkin's lymphoma, hairy cell lymphoma and Burkitt's lymphoma) as well as hematopoieitic tumours of myeloid lineage (for example acute myeloid leukaemia, chronic myeloid leukaemias, myelogenous leukaemias and Imatinib sensitive and refractory chronic myelogenous leukaemias, myelodysplastic syndrome, Bortezomib sensitive and refractory multiple myeloma, myeloproliferative disease or promyelocytic leukaemia and thyroid follicular cancer).

The invention finds application in the treatment of all sarcomas. Sarcoma refers to cancer that originates in supportive and connective tissues such as bones, tendons, cartilage, muscle and fat. Generally occurring in young adults, the most common sarcoma often develops as a painful mass on the bone. Sarcoma tumours usually resemble the tissue in which they grow. Exemplary sarcomas for treatment according to the invention include osteosarcoma (or osteogenic sarcoma); chondrosarcoma; leiomyosarcoma (smooth muscle); rhabdomyosarcoma (skeletal muscle); mesothelial sarcoma or mesothelioma (membranous lining of body cavities); fibrosarcoma (fibrous tissue); angiosarcoma or hemangioendothelioma (blood vessels); liposarcoma; glioma; astrocytoma: myxosarcoma (primitive embryonic connective tissue) and mesenchymous or mixed mesodermal tumour (mixed connective tissue types). Fibrosarcomas include peripheral nerve sheath tumours and other fibrous neoplasms, for example fibroblastic and myofibroblastic tumours, nerve sheath tumours and other fibromatous neoplasms. Also included is Kaposi sarcoma. Also included are soft tissue sarcomas, for example Ewing tumour and Askin tumour of soft tissue, pPNET of soft tissue, extrarenal rhabdoid tumour; fibrohistiocytic tumours; synovial sarcomas; osseous and chondromatous neoplasms of soft tissue and alveolar soft parts sarcoma. Osteosarcomas (malignant bone tumours) include: malignant fibrous neoplasms of bone; malignant chordomas and odontogenic malignant tumours. Gliomas include oligodendrogliomas, mixed and unspecified gliomas and neuroepithelial glial tumours.

The invention finds application in the treatment of cancers of the mixed type, including for example adenosquamous carcinoma, mixed mesodermal tumour, carcinosarcoma and teratocarcinoma. The invention therefore finds application in the treatment of various CNS. PNS and miscellaneous intracranial and intraspinal neoplasms, including: astrocytoma, neuroblastoma, glioma, schwannoma, ependymomas and choroid plexus tumour (for example ependymomas and choroid plexus tumours); intracranial and intraspinal embryonal tumours (for example medulloblastomas, primitive neuroectodermal tumour (PNET), medulloepithelioma, atypical teratoid/rhabdoid tumour and other intracranial and intraspinal neoplasms (for example pituitary adenomas and carcinomas, tumours of the sellar region (craniopharyngiomas), pineal parenchymal tumours, neuronal and mixed neuronal-glial tumours, meningiomas and intracranial and intraspinal neoplasms in general).

Thus, the invention finds particular application in the treatment of: intracranial and intraspinal germ cell tumours; intracranial and intraspinal germinomas; intracranial and intraspinal teratomas; intracranial and intraspinal embryonal carcinomas; intracranial and intraspinal yolk sac tumour, intracranial and intraspinal choriocarcinoma and intracranial and intraspinal tumours of mixed forms.

The invention also finds application in the treatment of various germ cell tumours, trophoblastic tumours and neoplasms of the gonads. Thus, the invention finds application in the treatment of malignant extracranial and extragonadal germ cell tumours include, for example, malignant germinomas of extracranial and extragonadal sites, malignant teratomas of extracranial and extragonadal sites, embryonal carcinomas of extracranial and extragonadal sites, yolk sac tumour of extracranial and extragonadal sites; choriocarcinomas of extracranial and extragonadal sites and malignant mixed germ cell tumours of extracranial and extragonadal sites in general. The invention also finds application in the treatment of malignant gonadal germ cell tumours, including for example malignant gonadal germinomas, seminomas, malignant gonadal teratomas, gonadal embryonal carcinomas, gonadal yolk sac tumour, gonadal choriocarcinoma, malignant gonadal tumours of mixed forms and malignant gonadal gonadoblastoma.

Infectious Disease

The compounds of the invention are sialidase inhibitors, and so find application in the treatment or prophylaxis of diseases and disorders mediated by sialidase activity and/or sialic acid. Such diseases and disorders include infectious diseases (including bacterial and viral infections).

The compounds of the present invention may have anti-infective (e.g. pathostatic or pathocidal) activity against any infective agent. The compounds of the invention may therefore target (i.e. have activity against) a wide range of different infectious agents. Thus, the invention finds broad application in the treatment or prevention of any infection or infectious disease, including infectious diseases in which viral, bacterial, fungal, protozoal, prion or metazoan agents are implicated.

Thus, the invention finds broad application in the treatment or prevention of viral infection; the treatment or prevention of bacterial infection: the treatment or prevention of protozoal infection; the treatment or prevention of fungal infection; the treatment or prevention of prion infection; and/or the treatment or prevention of metazoan (e.g. helminth) infection or infestation. The compounds of the invention may also find application in the treatment or prevention of chroni, dormant or latent viral, bacterial, protozoal, fungal, prion or metazoan (e.g. helminth) infections or infestations.

Viral targets include but are not limited to the following viruses (or virus classes): Retroviridae (e.g. the human immunodeficiency viruses, including HIV-1); Picornaviridee (e.g. polio viruses, hepatitis A virus; enteroviruses, human Coxsackie viruses, rhinoviruses, echoviruses); Calciviridae (e.g. strains that cause gastroenteritis); Togavirdae (e.g. equine encephalitis viruses, rubella viruses); Flaviride (e.g. dengue viruses, encephalitis viruses, yellow fever viruses); Coronoviridae (e.g. coronaviruses); Rhabdoviradae (e.g. vesicular stomatitis viruses, rabies viruses); Filovidae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); *Arena viridae* (hemorrhagic fever viruses); Reoviridae (e.g. reoviruses, orbiviurses and rotaviruses); Birnaviridae; Hepadnaviridae (Hepatitis B virus); Pavoviridae (parvoviruses); Papovaviridae (papilloma viruses, polyoma viruses); Adenoviridae (most adenoviruses): Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the HCV virus (causing non-A, non-B hepatitis); Norwalk and related viruses, and astroviruses). Of the foregeoing, particularly preferred are HIV, Hepatitis A, Hepatitis B, Hepatitis C, rabies virus, poliovirus, influenza virus, meningitis virus, measles virus, mumps virus, rubella, pertussis, encephalitis virus, papilloma virus, yellow fever virus, respiratory syncytial virus, parvovirus, chikungunya virus, haemorrhagic fever viruses and Herpes viruses, particularly, varicella, cytomegalovirus and Epstein-Barr virus.

Bacterial targets include but are not limited to both Gram-negative and Gram-positive bacteria. Examples of bacteria which may be targeted by the compounds of the invention include but are not limited to: *Helicobacter pylori, Borelia burgdorferi, Legionella pneumophilia, Mycobacterium* spp (e.g. *M. tuberculosis. M. leprae, M. avium, M. intracellulare, M. kansaii* and *M. gordonae), Staphylococcus aureus, Neisseria gonorrhoeae, Neisseria meningitidis, Listera monocytogenes, Streptococcus pyogenes* (Group A *Streptococcus), Streptococcus agalactiae* (Group B *Streptococcus), Streptococcus viridans. Streptococcus faecalis. Streptococcus bovis,* any anaerobic species of the genus *Streptococcus, Streptococcus pneumoniae, Campylobacter* spp., *Enterococcus* spp., *Haemophilus influenzae, Bacillus anthracis, Corynebacterium* spp. (including *C. diphtheriae), Erysipelothrix rhusiopathiae, Clostridium perfringens, Clostridium tetani, Enterobacter aerogenes, Klebsiella* spp (including *K. pneumoniae), Pasteurella multocida, Bacteroides* spp., *Fusobacterium nucleatum, Streptobacillus monilijormis, Treponema pallidkum, Treponema pertenue, Leptospira* spp., *Rickettsia* spp. and *Actinomyces* spp. (including *A. israelii).* Bacteria which form biofilms in vivo are particular targets of the compounds of the invention, and these include *Tannerella forsythia, Tannerella denticola, Porphyromonas gingivalis* and *Gardnerella vaginalis.*

Fungal targets include but are not limited to *Cryptococcus neoformans, Histoplasma capsulatum, Coccidioides immitis, Blastomyces dermatitidis, Chlamydia trachomatis* and *Candida albicans.*

Protozoal targets include but are not limited to *Plasmodium* spp. (including *Plasmodium falciparum, Plasmodium malariae, Plasmodium ovale* and *Plasmodium vivax), Toxoplasma* spp. (including *T. gondii* and *T. cruzii), Leishmania* spp., *Cryptosporidium* spp. (including *C. parvum), Cyclospora* spp. (including *C. cayetanensis), Entamoeba* (including *E. histolytica)* and *Giardia* spp. (including *G. lamblia).*

Metazoan targets include parasites or pathogens, such as helminths (e.g. *Schistosoma* spp.).

Inhibition of Bacterial Growth In Vivo

Sialidase activity is key to utilization of sialoconjugate sugars and is involved in host-pathogen interactions with bacteria. Glycoprotein-associated sialic acid has been proposed as a key in vivo nutrient source for *Tannerella forsythia* when growing in a biofilm (Roy, S., 2011, Microbiology, 157, 3195). The sialidase inhibitory properties of the compounds of the invention also find application in the inhibition of commensal and/or pathogenic bacterial growth in vivo, and in particular in disrupting host-bacterial cell interactions, including the inhibition or elimination of bacterial biofilms in a mammalian (e.g. human) host.

The compounds therefore find application in the treatment or prophylaxis of diseases and disorders mediated or characterized by the presence of bacterial biofilms (for example, sub-gingival plaque biofilms and musosal biofilms).

Such diseases include periodontal diseases, bacterial vaginosis and diseases caused by infection with *Tannerella forsythia, Tannerella denticola, Porphyromonas gingivalis* and *Gardnerella vaginalis* (the latter species being associated with bacterial vaginosis and pre-term birth).

Modulation of Commensal Bacterial Growth

The sialidase inhibitory properties of the compounds of the invention also find application in the modulation of the composition of the microbiota (and in particular commensal bacteria) in a host, for example modulating the composition of commensal bacteria in mammalian (e.g. human) hosts. Particularly preferred is modulation of the gut microbiota.

Atherogenesis

The compounds of the invention are sialidase inhibitors, and so find application in the treatment or prophylaxis of atherogenesis, since sialidases are involved in this process (Sukhorukov, V. N., et al., 2017, Curr. Pharm. Des., 23, 4896) and osteo-arthritis (Katoh, S., et al., 1999, J Immunol., 162, 5058). Thus, the compounds of the invention find application in the treatment and prophylaxis of atherosclerosis.

Inflammation

The compounds of the invention inhibit sialidases which are thought to be involved in the TNF-$\alpha$ induced inflammatory process in osteo-arthritis (Gee, K. et al., 2003, J Biol Chem. 278, 37275). Furthermore, the compounds of the invention can suppress or inhibit TNF-$\alpha$ activity. As such, they find application in any disorder in which inflammation plays a role in the impairment of physiological function and/or symptoms and/or pain. For example, the compounds of the invention may be used as anti-inflammatories, for example to reduce or eliminate acute, chronic, local or systemic inflammation.

Inflammation occurs when tissues are injured by microorganisms, trauma, chemicals, heat, cold, sunburn or any other harmful events. Endogenous chemicals (for example, bradykinin, histamine and serotonin) are released on injury or insult, and such chemicals activate and attract tissue macrophages and other white blood cells. During this process, chemical mediators such as TNF-$\alpha$ are released, giving rise to inflammation.

Inflammatory disorders are those in which the inflammation is sustained or chronic. In such circumstances, prolonged inflammation causes tissue destruction and results in extensive damage and eventual failure of the effected tissue and/or organ.

Thus, the compounds of the invention find application in the treatment of non-localized inflammatory disorders, for example those affecting more than one organ. Such disorders include those arising from immune dysfunction (and may therefore have an autoimmune component). Such conditions include systemic lupus erythematosus (SLE), scleroderma and hypersenstivities.

There is a growing body of evidence linking inflammation to the development of type 2 diabetes.

The compounds of the invention also find application in the treatment of localized inflammatory disorders, including skin inflammation and chronic prostatitis, glomerulonephritis, inflammatory bowel diseases, pelvic inflammatory disease, reperfusion injury, rheumatoid arthritis, transplant rejection, vasculitis, asthma, acne, osteoarthritis, oral mucosal, gastrointestinal inflammation, ocular, nasal and aural inflammation and other steroid responsive inflammatory disorders.

In particular, the compounds of the invention find application in the treatment of cutaneous inflammatory diseases. These include, for example, actinic keratosis, acne (including acne vulgaris, comedonal, acne rosacea, and nodulocystic acne), allergic contact dermatitis, angioedema, bullous pemiphigoid, cutaneous drug reactions, erythema multiforme, lupus erythrametosus, photodermatitis, psoriatic arthritis, scleroderma and urticaria, psoriasis, dermatitis (e.g. atopic dermatitis), scleroderma, steroid-responsive cutaneous inflammatory disorders (for example uremic pruritus) and skin conditions associated with exposure to sun, radiation, chemotherapy and environmental irritants.

The compounds of the invention also find application in the treatment of inflammatory autoimmune diseases. Such diseases may involve specific tissues or organs (such as the musculoskeletal tissue, as in rheumatoid arthritis and ankylosing spondylitis), the GI tract (as for example in Crohn's disease and ulcerative colitis), the CNS (as for example in Alzheimer's disease, multiple sclerosis, motor neurone disease, Parkinson's disease and chronic fatigue syndrome), pancreatic beta cells (for example insulin-dependent diabetes mellitus), the adrenal gland (for example Addison's disease), the kidney (for example Goodpasture's syndrome. IgA nephropathy and interstitial nephritis), exocrine glands (for example Sjogren's syndrome and autoimmune pancreatitis) and the skin (for example psoriasis and atopic dermatitis).

Other inflammatory disorders treatable according to the present invention include conditions such as osteoarthritis, periodontal disease, diabetes (including type 2 diabetes and diabetic nephropathy), chronic obstructive pulmonary disease, artherosclerosis, graft versus host disease, chronic pelvic inflammatory disease, endometriosis, chronic hepatitis and tuberculosis.

Posology

The compositions and compounds of the present invention can be administered topically or by oral or parenteral routes, including intravenous, intramuscular, intraperitoneal, subcutaneous, transdermal, airway (aerosol), rectal, vaginal and topical (including buccal and sublingual) administration.

The amount administered can vary widely according to the particular dosage unit employed, the period of treatment, the age and sex of the patient treated, the nature and extent of the disorder treated, and the particular compound selected.

In general, the effective amount of the compound administered will generally range from about 0.01 mg/kg to 500 mg/kg daily. A unit dosage may contain from 0.05 to 500 mg of the compound, and can be taken one or more times per day. The compound can be administered with a pharmaceutical carrier using conventional dosage unit forms either orally, parenterally, or topically, as described below.

The preferred route of administration is oral administration. In general a suitable dose will be in the range of 0.01 to 500 mg per kilogram body weight of the recipient per day, preferably in the range of 0.1 to 50 mg per kilogram body weight per day and most preferably in the range 1 to 5 mg per kilogram body weight per day.

The desired dose is preferably presented as a single dose for daily administration. However, two, three, four, five or six or more sub-doses administered at appropriate intervals throughout the day may also be employed. These sub-doses may be administered in unit dosage forms, for example, containing 0.001 to 100 mg, preferably 0.01 to 10 mg, and most preferably 0.5 to 1.0 mg of active ingredient per unit dosage form.

Formulation

When isolated from a natural source, the idoBR1 may be purified. However, the compositions of the invention may take the form of herbal medicines, food supplements, food additives, nutraceuticals, beverages or unitary doses as a herbal pharmaceutical kit or pack as hereinbefore defined. Such herbal medicines preferably are analysed to determine whether they meet a standard specification prior to use.

The herbal medicines for use according to the invention may be dried plant material. Alternatively, the herbal medicine may be processed plant material, the processing involving physical or chemical pre-processing, for example powdering, grinding, freezing, evaporation, filtration, pressing, spray drying, extrusion, supercritical solvent extraction and tincture production. In cases where the herbal medicine is administered or sold in the form of a whole plant (or part thereof), the plant material may be dried prior to use. Any convenient form of drying may be used, including freeze-drying, spray drying or air-drying.

Compounds of the invention may be separated from the higher molecular weight components such as proteins and polysaccharides by extraction in polar solvents (such as ethanol/water mixtures, for example 250% v/v (e.g. up to ~70% v/v) ethanol/water mixtures). Other suitable techniques include various membrane technologies. These include microfiltration, ultrafiltration and nanofiltration. Alternatively, or in addition, electrodialysis may also be used to concentrate the charged compound. These methods use membranes of pore sizes that allow only molecules below a certain size to pass or rely on charges on the molecules to allow or not allow them to pass through the membrane. Anion and cation exchange resins may also be used to concentrate the compounds.

When isolated from a natural source, the compound for use according to the invention may be purified. In embodiments where the compound is formulated together with a pharmaceutically acceptable excipient, any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc.

The pharmaceutical compositions may take any suitable form, and include for example tablets, elixirs, capsules, solutions, suspensions, powders, granules and aerosols.

The pharmaceutical composition may take the form of a kit of parts, which kit may comprise the composition of the invention together with instructions for use and/or a plurality of different components in unit dosage form.

Tablets for oral use may include the compound for use according to the invention, mixed with pharmaceutically acceptable excipients, such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the compound for use according to the invention is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

For oral administration the compound or compounds can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch.

In another embodiment, the compounds of the invention are tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, colouring agents, and flavouring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The compounds of the invention may also be administered parenterally, that is, subcutaneously, intravenously, intramuscularly, or interperitoneally.

In such embodiments, the compound is provided as injectable doses in a physiologically acceptable diluent together with a pharmaceutical carrier (which can be a sterile liquid or mixture of liquids). Suitable liquids include water, saline, aqueous dextrose and related sugar solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as poly(ethylene-glycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carhomers, methylcellulose, hydroxypropylmethylcellulose, or carboxymethylcellulose), or emulsifying agent and other pharmaceutically adjuvants. Suitable oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate.

Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulphonates, alkyl, olefin, ether, and monoglyceride sulphates, and sulphosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the compound for use according to the invention in solution. Preservatives and buffers may also be used. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compound or compounds for use according to the invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the compound from about 0.1 to about 10% w/v (weight per unit volume).

When used adjunctively, the compound or compounds for use according to the invention may be formulated for use with one or more other drug(s). Thus, adjunctive use may be reflected in a specific unit dosage designed to be compatible (or to synergize) with the other drug(s), or in formulations in which the compound or compounds are admixed with one or more enzymes. Adjunctive uses may also be reflected in the composition of the pharmaceutical kits of the invention, in which the compounds of the invention is co-packaged (e.g. as part of an array of unit doses) with the enzymes. Adjunctive use may also be reflected in information and/or instructions relating to the co-administration of the compound or compounds and/or enzyme.

Cosmetic Formulations

The cosmetic compositions of the invention may be selected for example from moisturizing compositions, cleansing compositions, or any composition that may provide a benefit to the skin. The cosmetic compositions of the invention may comprise cosmetically-acceptable excipients or carriers, for example selected from those described below.

In one embodiment, the cosmetic composition is a cleansing composition. Suitable cleansing compositions are solid or semi-solid at room temperature. Examples of useful cleansing compositions include, but are not limited to, fatty acid soaps, including glycerin soaps, synthetic detergents and mixtures thereof. Solid cleansing compositions are extensively taught in Soap Technology for the 1990's, the contents of which are incorporated herein by reference. It is desirable that the cleansing composition be flowable.

In one embodiment of the invention, the cleansing composition comprises glycerin soap. Examples of glycerin soaps useful in the present invention include but are not limited to those disclosed in U.S. Pat. Nos. 4,405,492 and 4,879,063, the disclosures of which are hereby incorporated by reference.

Examples of suitable fatty acid soaps include soaps derived from hydrocarbon chain lengths of from approximately 10 to 22 (including carboxyl carbon) and may be saturated or unsaturated. The soap may be, for example, the sodium salt, potassium salt, ammonium salt, triethanolammonium salt and mixtures thereof.

Suitable synthetic detergents include those known in the art for the desired purpose. Examples of detergents useful for personal cleansing include the isethionates, sarcosinates, and glyceryl ether sulfonates which may be pure chain length variants or those derived from commercial oils such as coconut oil. Other suitable detergents include anionic acyl sarcosinates, methyl acyl taurates, N-acyl glutamates, alkyl sulphosuccinates, alkyl phosphate esters, ethoxylated alkyl phosphate esters, trideceth sulphates, protein condensates, mixtures of ethoxylated alkyl sulphates and alkyl amine oxides, betaines, sultaines and mixtures thereof. Included are the alkyl ether sulphates with 1 to 12 ethoxy groups, especially ammonium and sodium lauryl ether sulphates.

The cosmetic composition may be a moisturizing composition.

Other optional components of the cosmetic compositions of the invention include, but are not limited to, perfumes, fragrances, preservatives, colourants, dyes, anti-caking agents, and personal care ingredients, including, but are not limited to, skin and hair care ingredients.

Examples of suitable personal care ingredients useful in the present invention include but are not limited to safe and effective amounts of: humectants, sunscreen actives, skin soothers, anti-irritants, anti-inflammatories, emollients, conditioning agents, moisturizers, deodorants, anti-perspirants, artificial tanning agents, antimicrobial agents, anti-acne agents, anti-wrinkle agents, anti-skin atrophy agents, skin firming agents, anti-itch agents, anti-fungal agents, topical anaesthetics, skin tone evening agents, active natural ingredients, agents for minimizing the appearance or retarding regrowth of unwanted hair, skin texture modifiers, and additional cleansing agents.

In one embodiment the compound may be used from a water or alcoholic water extract by using a water in oil (w/o) emulsion such as are employed for example in the treatment of dry skin and emollient applications Emollients function by their ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 cetyl ether, steareth-10, oleth-8, PPG-4 lauryl ether, vitamin E acetate, PEG-7 glyceryl cocoate, lanolin, and combinations thereof. Vitamin E acetate, PEG-7 glyceryl cocoate and combinations thereof are preferred.

Examples of suitable humectants include polyhydric alcohols. Suitable polyhydric alcohols include, but are not limited to, glycerol (also known as glycerin), polyalkylene glycols, alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof.

Suitable skin soothers include, but are not limited to, panthenol, bisabolol, allantoin, aloe, and combinations thereof.

Suitable conditioning agents include, but are not limited to, dimethicone propyl PG-betaine, dimethicone copolyols, polyquaternium-10, guar, guar derivatives, and combinations thereof. Suitable anti-acne active ingredients include, but are not limited to, salicylic acid, sulphur, lactic acid, glycolic acid, pyruvic acid, urea, resorcinol, N-acetylcysteine, retinoic acid, benzoyl peroxide, octopirox, triclosan, azelaic acid, phenoxyethanol, phenoxypropanol, flavonoids, derivatives thereof, and combinations thereof. Salicylic acid and benzoyl peroxide arE preferred.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1: Sialidase Inhibition by idoBR1

Introduction

Sialidases or neuraminidases are enzymes that catalyze the cleavage of terminal sialic acids from oligosaccharides and glycoconjugates. They play important roles in regulating metabolism of sialic acid-containing molecules in biological systems. They are also virulence factors for many viruses and pathogenic bacteria such as *Tannerella forsythia*. Sialidase activity of human neutrophils is reported to play a critical role in the host inflammatory response (Glanz, V. Y., 2019. European J. Pharmacol. 842, 345).

Methods.

Sialidase assays used 2.8 mM and 0.28 mM inhibitor (or water without inhibitor) and 2.5 nM sialidase (including NanH from *T. forsythia*) incubated in the presence of 0.1 mM methylumbelliferyl-N-acetyineuraminic acid, pH 7.2 in 20 mM sodium phosphate buffer. Reactions were stopped at 30 seconds and 60 seconds via addition of pH 10.5 60 mM sodium carbonate buffer. Release of fluorogenic methylumbelliferone (MU) was quantified by measuring fluorescence emission at 450 nm, excitation 350 nm. Percentage sialidase activity was expressed as the change in fluorescence between 30 seconds and 60 seconds compared to that of a reaction without inhibitor. Reactions were carried out in triplicate.

Results idoBR1 gave inhibition of the sialidase which was not clearly dose dependent with over 30% inhibition at both concentrations used (2.8 mM [36%] and 0.28 mM [42%]).

The similar inhibitions seen at both concentrations suggest that the inhibition is not competitive.

Example 2: Inhibition of Endogenous Sialidase Activity Assay in THP-1 Cells

Introduction

The purpose of this study was to determine if idoBR1 or cucumber extract (Q-actin batch B17CF001) with over 1% idoBR1 could affect the activity of sialidase in human THP-1 (monocyte-like) cell cultures. The result of this study could be a combination of reduced expression of sialidase or inhibition of the enzyme by the idoBR1.

Method

THP-1 Cell Line Treatment for Sialidase Activity Test

The THP-1 cells were cultured in RPMI media supplemented with mercaptoethanol & glutamine to get 80% confluence in culture flask, then aspirated and centrifuged at 1500 rpm for 5 mins. The cell pellet was then resuspended in 1 ml of RPMI complete media and counted conventionally using a Hemocytometer. The cells (5×106) were incubated with PMA (10 ng/ml) in separate dishes to differentiate THP-1 cells. To determine the sialidase activity, THP-1 cells were pretreated for 1 hr with idoBR1 and Cucumber extract-Q-actin (batch no. B17CF001) at the concentrations 100 µg/ml to 12.5 µg/ml and 200 µg/ml to 25 µg/ml respectively followed by 24 hr LPS (1 µg/ml stimulation. Post incubation, the cells were used to determine the sialidase activity.

The THP-1 cells were washed with phosphate-buffered saline (PBS) and resuspended in ice-cold buffer containing 0.25 M sucrose, 1 mM EDTA, and 0.2 mM phenylmethylsulfonyl fluoride. The cell suspension was sonicated on ice for 15 s on a low setting (6% amplitude) (Vibracell™; Sonics and Materials Inc., Newtown, CT) followed by centrifugation at 25,000 g for 15 min at 4° C. The resulting supernatant was used to determine the lysosomal sialidase activity. Protein quantification of the supernatant was performed using the Bio-Rad protein determination kit as described above. For the determination of lysosomal sialidase activity, 200 µg of total protein was mixed with 40 nmol of 4-methylumbelliferyl-α-N-acetyl-D-neuraminic acid (Sigma), the lysosomal sialidase-specific substrate, 10 µmol sodium acetate buffer, pH 4.6, and 200 µg of bovine serum albumin in a total volume of 200 µl. The sialidase reaction was allowed to proceed for 1 h at 37° C. and was terminated by the addition of 0.25 M glycine NaOH, pH 10.4. Released 4-methylumbelliferone was measured fluorometrically (Synergy 2 multimode microplate reader) at an excitation wavelength of 365 nm and emission wavelength of 448 nm. The sialidase activity was found to be maximum at the 16 hour cell incubation time point.

Results

Inhibition of Endogenous Sialidase Activity by IdoBR1

| Sample | Concentration µg/ml | Sialidase activity/mg of protein Time in hours | | | |
|---|---|---|---|---|---|
| | | 4 | 8 | 16 | 24 |
| Media control | 0 | 8.51 | 6.45 | 7.29 | 4.09 |
| LPS (1 µg/ml) | LPS | 100.00 | 154.17 | 208.33 | 125.00 |
| IdoBR1 | 12.5 µg/mL + LPS | 91.30 | 129.95 | 186.34 | 108.47 |
| | 25 µg/mL + LPS | 86.48 | 121.84 | 178.24 | 103.85 |
| | 50 µg/mL + LPS | 79.35 | 109.77 | 130.21 | 88.83 |
| | 100 µg/mL + LPS | 72.15 | 99.32 | 115.16 | 78.66 |

Inhibition of Endogenous Sialidase Activity by Cucumber Extract Batch No. B17CF007 (Q-Actin)

| Sample | Concentration µg/ml | Sialidase activity/mg of protein Time in hours | | | |
|---|---|---|---|---|---|
| | | 4 | 8 | 16 | 24 |
| Media control | 0 | 8.51 | 6.45 | 7.29 | 4.09 |
| LPS (1 µg/ml) | LPS | 100.00 | 154.17 | 208.33 | 125.00 |
| Cucumber extract B17CF007 | 25 µg/mL + LPS | 95.47 | 134.05 | 199.07 | 114.11 |
| | 50 µg/mL + LPS | 88.94 | 124.25 | 187.50 | 109.16 |
| | 100 µg/mL + LPS | 81.80 | 113.87 | 145.83 | 92.82 |
| | 200 µg/mL + LPS | 74.10 | 102.92 | 128.47 | 75.46 |

The sialidase activity was found to be highest at the 16 hr time points post LPS (1 µg/mL) treatment and so this incubation time was used for further evaluation of the effects of the idoBR1 and cucumber extract on sialidase activity in the THP-1 cells.

Relative Sialidase Activity in THP-1 Cells Treated with Test Samples for 2 Hrs Followed by 16 Hours LPS Stimulation by IdoBR1

| Sample | Conc. µg/ml | RFU | Sialidase activity/ mg protein | Relative sialidase activity/ mg protein |
|---|---|---|---|---|
| Media control | 0 | 63 | 7.29 | 0.04 |
| LPS 1 µg/ml | | 1800 | 208.33 | 1.00 |
| idoBR1 | 12.5 | 1610 | 186.34 | 0.89 |
| | 25 | 1540 | 178.24 | 0.86 |
| | 50 | 1125 | 130.21 | 0.63 |
| | 100 | 995 | 115.16 | 0.55 |

Relative Sialidase Activity in THP-1 Cells Treated with Test Samples for 2 Hrs Followed by 16 Hours LPS Stimulation by Cucumber Extract Batch No. B17CF007 (Q-Actin)

| Sample | Conc. µg/ml | RFU | Sialidase activity/ mg protein | Relative sialidase activity/ mg protein |
|---|---|---|---|---|
| Media control | 0 | 63 | 7.29 | 0.04 |
| LPS 1 µg/ml | | 1800 | 208.33 | 1.00 |
| Cucumber extract | 25 | 1720 | 199.07 | 0.96 |
| | 50 | 1620 | 187.50 | 0.90 |
| | 100 | 1260 | 145.83 | 0.70 |
| | 200 | 1110 | 128.47 | 0.62 |

The standard idoBR1 tested at 50 µg/ml and 100 µg/ml showed maximum reduction in relative sialidase activity 0.63 and 0.55 respectively compared to LPS control. Q-actin at 100 µg/ml and 200 µg/ml showed maximum reduction of relative sialidase activity to 0.7 and 0.62 respectively compared to control (LPS).

Example 3: THP-1 Cell Line Treatment for CD44-HA (Hyaluronic Acid) Binding Activity in the Presence of idoBR1 Using EUSA Introduction CD44 has been shown to be involved in hemopoiesis, homing to mucosal lymphatic tissue, and lymphocyte infiltration into inflammatory tissues. Hyaluronic acid (HA)

interactions with CD44 and CD168 (RHAMM) can induce numerous cell behaviours, including activation of tyrosine kinases, protein kinase C, FAK, and PI3K, MAPK, NFκB, and RAS, as well as cytoskeletal components required for inflammation and cancer. Although most cells express some form of CD44, not all cells constitutively bind HA (Kryworuchko, M. et al., 1999, Cellular Immunol., 194, 54, Nandi et al., 2000, J. Biol. Chem., 275, 14939). Functionally active HA adhesive CD44 is produced through induction of sialidase via MAPK activation. Studies carried out to understand the role of MAPK in the LPS induced inflammatory response has shown MAPK p42/44 mediated TNF-α production and subsequent TNF-α mediated p38 activation resulting in production of HA adhesive CD44 by sialidase activity (Gee, K. et al., 2003, J Biol Chem. 278, 37275).

Methods

The THP-1 cells were cultured in RPMI media supplemented with mercaptoethanol & glutamine to get 80% confluence in the culture flask, then aspirated and centrifuged at 1500 rpm for 5 mins. The cell pellet was then resuspended in 1 ml of RPMI complete media and counted conventionally using a hemocytometer. The cells (5×106) were incubated with Phorbol 12-myristate 13-acetate (PMA) (10 ng/ml) in separate dishes to cause differentiation of the THP-1 cells. To determine the CD44-HA binding activity, THP-1 cells were pretreated for 1 hr with idoBR1 or cucumber extract-Q-actin (batch no. B17CF001) at the concentrations 100 μg/ml to 12.5 μg/ml and 200 μg/ml to 25 μg/ml respectively followed by 24 hr LPS (1 μg/ml) stimulation. Post incubation, the cell lysates were taken for further analysis.

Anti-CD44 monoclonal antibody (Invitrogen, 2 μg) was coated to each well in 96-well plates in 50 mM carbonate/bicarbonate buffer (pH 9.6) and incubated overnight at 4° C. The unbound antibodies were removed using PBS with 0.05% Tween 20 (PBS-T wash solution). The wells were blocked using 1% BSA and incubated for 1 hr at 37° C. The wells were washed thrice thoroughly using PBS-T wash solution by adding 200 μl into wells. 50 μl cell lysates were added to the wells and incubated for 1 hr at 37° C. The wells were then washed thrice by adding 200 μl of PBS-T by soaking the wells for 30 secs before each wash. Biotinylated-Hyaluronic acid (HA) antibody followed by Streptavidin-HRP was added to form an immune complex and incubated for 60 mins at 37° C. The solution was aspirated and the wells washed thrice with 200 μl wash solution by soaking the wells for 30 secs. 50 μl of both Chromogen A and Chromogen B was added to each well. The plate was incubated for 15 mins away from light at 37° C. The reaction was stopped by adding 50 μl Stop Solution and the absorbance was read at 450 nm.

Results

Inhibition of CD44-HA Binding by IdoBR1

| Sample | Conc. μg/mL | CD44-HA (ng/mL) | % reduction in CD44-HA levels |
|---|---|---|---|
| control | LPS | 110.45 | 0.00 |
| idoBR1 | 12.5 | 101.48 | 8.12 |
| | 25 | 94.93 | 14.05 |
| | 50 | 88.43 | 19.93 |
| | 100 | 81.04 | 26.62 |

Inhibition of CD44-HA Binding by Cucumber Extract Batch No. B17CF007 (QActin)

| Sample | Conc. μg/mL | CD44-HA (ng/mL) | % reduction in CD44-HA levels |
|---|---|---|---|
| control | LPS | 110.45 | 0.00 |
| Cucumber | 12.5 | 103.13 | 6.63 |
| extract | 50 | 97.78 | 11.47 |
| | 100 | 89.52 | 18.95 |
| | 200 | 76.65 | 30.60 |

The CD44 bound HA was found to be 110.45 ng/ml in LPS-stimulated (1 μg/ml) (THP-1 cells. Ido-BR1 at 100 μg/ml exhibited the highest reduction of CD44-HA levels (26.62%) in the LPS-induced inflammatory response in THP-1 cells as compared to the LPS control. Cucumber extract-Q-actin at 200 μg/ml showed the highest reduction of CD44-HA levels (30.60%) in the LPS induced inflammatory response in THP-1 cells as compared to LPS control.

Example 4: Reduction of TNF-Alpha Production by idoBR1 and Q-Actin Cucumber Extract in Human Blood Introduction TNF-α, a cytokine produced by monocytes (macrophages) and T lymphocytes, is a key element in the cascade of factors that produce the inflammatory response and has many pleiotropic effects as a major orchestrator of disease states (Beutler, B. et al., 1989, Annual Review of Immunology, 7, 625). The biological effects of TNF-α depend on its concentration and site of production: at low concentrations, TNF-α may produce desirable homeostatic and defense functions, but at high concentrations, systemically or in certain tissues, TNF-α can synergize with other cytokines, notably interleukin-1 (IL-1) to aggravate many inflammatory responses. The aim of this study was to evaluate the anti-inflammatory activity of idoBR1 or cucumber extract with idoBR1 with respect to the ability to modulate TNF-α levels in whole human blood.

Methods

Blood and buffy coat fractions were supplied by the Scottish National Blood Transfusion Service (SNBTS), Glasgow, UK. Ficoll Histopaque (1.077 g/l), Lipopolysaccharide (from *Salmonella abortus equi*) was purchased from Sigma-Aldrich Co. Ltd. (UK). PGE was from Cayman Chemical Co. (Ann Arbor, MI). Human TNF-α antibody pairs for TNF-α ELISA assays was from Invitrogen/Life Sciences Europe. All drugs were dissolved in RPMI 1640 medium from Gibco BRL, UK.

Blood was used without any further treatment following donation. It was kindly supplied by the Scottish National Blood Transfusion Service from normal healthy donors as defined by ensuring they all tested negative for HIV, hepatitis B & C, CMV and parasitic diseases such as malaria (as tested by the National Blood Transfusion service). They were also confirmed by our laboratory to be free of acute inflammatory disease at the time the blood was taken by measuring the basal level of TNF-α which was always <50 μg/ml.

Stimulation of Cells and Measurement of TNF-α

Aliquots (800 μl) of whole blood were incubated with the compound dissolved in RPMI 1640, as indicated in the results, for the appropriate preincubation period after which LPS was added and incubations continued for a further 20 hr at 37° C. in a humidified (100%) atmosphere of 5% $CO_2$ in air. At the end of the incubation period, supernatants from either plasma or culture medium were collected by centrifugation at 10,000 g for 30 seconds at room temperature and TNF-α levels measured using a human TNF-α ELISA system (BioSource Europe S.A., Belgium, supplied by Invitrogen).

Results

Strong activity of cucumber extract and idoBR1 on LPS-induced TNF-α in human blood is shown in the following two tables. It is shown that the cucumber extract (pilot Q-actin) containing idoBR1 at 0.09% reduces the TNF-α, while idoBR1 is effective at well below 10 μM and confirming idoBR1 alone can be responsible for the anti-inflammatory effect of cucumber extract. Q-actin contains 10-100 times more idoBR1 than that in the pilot extract used here. Q-actin extract with 10 fold less idoBR1 had a 10 fold lesser effect on TNF-α (data not shown).

A second study indicated even greater activity for idoBR1 in human blood (significant at 0.01 μM) with pre-incubation. The $IC_{50}$ for idoBR1 with 48 hr preincubation was calculated as 182 nM for blood and 27 nM for inhibition of the production of TNF-α by human monocytic cell line THP-1 cells. idoBR1 did not significantly alter the viability of THP-1 cells as measured by trypan blue uptake or MTT dye conversion. The inhibitory action of idoBR1 (at 10 μM) was comparable to that of identical pretreatment with dexamethasone (50 μM) with an inhibition of >50% and >65% respectively. Mifepristone (a glucocorticoid receptor antagonist) alone with LPS greatly amplified TNF-α production from THP-1 cells, however, in the presence of dexamethasone it reversed the suppressive action of dexamethasone but not that of idoBR1. The data clearly indicate that idoBR1 can inhibit the production of TNF-α in human blood. Thus, it appears that it may be a potent anti-inflammatory agent. It also appears that it may be acting via a novel mechanism distinct from the steroid receptor pathways.

Table showing the effect of various idoBR1 concentrations on LPS-stimulated TNF-α production in human blood. Whole blood was preincubated for 48 h with varying concentrations of idoBR1 after which LPS (10 μg/ml) was added and incubations continued for a further 20 h. Following incubation at 37° C. (5% $CO_2$, 100% humidity) plasma was collected from blood by centrifugation and the levels of TNF-α In plasma samples were measured by ELISA.

| idoBR1 μM | 0 | 0.01 | 0.1 | 1 | 10 |
|---|---|---|---|---|---|
| TNF-α pg/ml plasma (no LPS) | 200 | | | | 200 |
| TNF-α pg/ml plasma + LPS | 1650 | 1680 | 950* | 490* | 500* |

Values represent the means ± s.d. of n = 3.
*denotes P < 0.05 compared to LPS alone (zero idoBR1).

Table showing the effect of various cucumber extract (0.09% idoBR1) concentrations on LPS-stimulated TNF-α production in human blood. Whole blood was preincubated for 48 h with varying concentrations of cucumber Q-Actin extract after which LPS (10 μg/ml) was added and incubations continued for a further 20 h. Following incubation at 37° C. (5% $CO_2$, 100% humidity) plasma was collected from blood by centrifugation and the levels of TNF-α in plasma samples were measured by ELISA. Values represent the means±s.d. of n=3. * denotes P<0.05 compared to LPS alone.

| Cucumber extract concn mg/ml | 0 | 0.02 | 0.2 | 2 |
|---|---|---|---|---|
| TNF-α pg/ml plasma (no LPS) | 200 | | | 200 |
| TNF-α pg/ml plasma + LPS | 1650 | 1750 | 1250* | 650* |

Example 5: Effects of IdoBR1 and Cucumber Extract on Cytokines IL-10, IL-12 and IL-1β in LPS Stimulated THP-1 Cells Introduction IL-10 is an anti-inflammatory cytokine and an important negative regulator of proinflammatory cytokines. A variety of cell types, including T cells, B cells, and monocytes/macrophages secrete IL-10 under different conditions of immune activation (Moore, K. et al., 1993, Annu. Rev. Immunol., 11, 165). In vitro studies have shown that IL-10 suppresses the release and function of IL-1β, IL-6, TNF-α, granulocyte macrophage colony-stimulating factor, and IL-12 (Casatella. M. et al., 1993. J. Exp. Med., 178, 2207; de Waal Malefyt, R. et al., 1991, J. Exp. Med., 174, 1209; Fiorentino, D. et al., 1991, J. Immunol., 147, 3815), thereby suggesting a normal endogenous feedback mechanism for the control of immune responses and inflammation (Asadullah, K. et al., 1998, J. Clin. Invest. 101, 783; Joosten, L. et al., 1997, Arthritis Rheum., 40, 249). Studies have demonstrated that IL-10 exerts its suppressive effect on IL-12 p40 and p35 as well as on TNF-a gene expression mainly at the transcriptional level (Aste-Amezaga, M. et al., 1998, J. Immunol., 160, 5936). Among the pro-inflammatory cytokines that are involved in the pathogenesis of several autoimmune diseases, IL-12 is the main stimulator of IFN-γ production and of the development of T helper (Th) 1 autoimmune responses (Paunovic, V. et al., 2008, Rheumatology, 47, 771). It has been documented that IL-12 synergizes with a variety of cytokines and induces the production of IFN-γ and proinflammatory cytokines. Monocytes/macrophages produce IL-1β along with TNF-α which mediate inflammation upon infection or by stimulation of LPS. It induces inflammatory reactions and catabolic effect independently as well as being combined with other mediators. The biological activation of cells by IL-1β is mediated by interaction with the membrane receptor, namely, the IL-1R1 (IL-1RI, CD121a), which can also bind IL-1α, another IL-1 group.

Methods

ELISA Assay on THP-1 Monocytes

Sample Preparation for ELISA Assay

The cells in an 80% confluence culture flask were aspirated and centrifuged at 1500 rpm for 5 mins. The cell pellet was then resuspended in 1 ml of RPMI complete media and 1×10 5 cells/well seeded to each well of the 96 well microtiter plate. After 24 hrs incubation, PMA (10 ng/ml) was added to the 96 well plate to differentiate THP-1 cells to determine the TNF-α production, THP-1 cells were pretreated for 1 hr with idoBR1 or cucumber extract-Q-actin (batch no. B17CF001) at the concentrations 200 μg/ml to 25 μg/ml diluted two fold serially followed by 2 hr LPS (100 ng/m) stimulation. Post incubation, the cell supernatant from each of the wells was aspirated into sterile micro centrifuge tubes and centrifuged at 1000 rpm for 2-3 mins. The cell supernatant was then used for evaluation of presence of cytokines using ELISA.

Sandwich ELISA Assay

ELISA plates coated with antibodies for IL-12, IL-1β, or IL-10 (R&D Systems, USA) were used for the following study. To each well 50 μL of Assay Diluent RD1F was added after mixing well. 200 μL of sample (idoBR1 or extract), or control per well was added and covered with an adhesive strip. Following incubation for 2 hours at room temperature each well was aspirated and washed 4 times with Wash Buffer (400 μl). After the last wash, any remaining Wash Buffer was removed by aspirating or decanting. The plates were inverted and blotted against clean paper towels. To each well 200 μl of appropriate human conjugate was added and these then covered with a new adhesive strip and incubated for 1 hour at room temperature. The aspiration/wash was then repeated. 200 μL of Substrate Solution was then added to each well and further incubated for 20 minutes at room temperature protected from light. 50 μL of Stop Solution was added to each well. The colour in the wells was changed from blue to yellow. OD was measured within 30 minutes at 450 nm.

Results

| Sample | Conc. μg/mL | IL-10 (pg/mL) | Fold increase in IL-10 levels |
|---|---|---|---|
| Control | 0 | 14.16 | 1.00 |
| idoBR1 | 12.5 | 19.02 | 1.34 |
|  | 25 | 29.34 | 2.07 |
|  | 50 | 37.22 | 2.63 |
|  | 100 | 43.08 | 3.04 |
| Control | 0 | 14.16 | 1.00 |
| Cucumber | 25 | 23.08 | 1.63 |
| extract Batch | 50 | 31.36 | 2.21 |
| B17CF007 | 100 | 36.38 | 2.60 |
|  | 200 | 51.68 | 3.65 |

Reduction in IL-12 at Different Conc. Of IdoBR1

| Sample | Conc. μg/mL | IL-12 (pg/mL) | % reduction in IL-12 levels |
|---|---|---|---|
| LPS Control | 0.1 | 117.4 | 0.00 |
| IdoBR1 | 12.5 | 104.23 | 11.22 |
|  | 25 | 97.37 | 17.07 |
|  | 50 | 92.89 | 20.88 |
|  | 100 | 88.60 | 24.53 |

Reduction in IL-12 at Different Conc. Of Cucumber Extract (Batch No. B17CF007)

| Sample | Conc. μg/mL | IL-12 (pg/mL) | % reduction in IL-12 levels |
|---|---|---|---|
| LPS Control | 0.1 | 117.4 | 0.00 |
| Cucumber | 25 | 102.74 | 12.49 |
| extract Batch | 50 | 95.95 | 18.27 |

-continued

| Sample | Conc. μg/mL | IL-12 (pg/mL) | % reduction in IL-12 levels |
|---|---|---|---|
| B17CF007 | 100 | 89.60 | 23.68 |
|  | 200 | 87.02 | 25.88 |

Reduction in IL-1β at Different Conc. of IdoBR1

| Sample | Conc. μg/mL | IL-1β (pg/mL) | % reduction in IL-1 β levels |
|---|---|---|---|
| LPS Control | 0.1 | 146.89 | 0.00 |
| IdoBR1 | 12.5 | 133.30 | 9.31 |
|  | 25 | 127.63 | 13.17 |
|  | 50 | 120.36 | 18.12 |
|  | 100 | 111.60 | 24.07 |

Reduction in IL-1β at Different Conc. Of Cucumber Extract (Batch No. B17CF000

| Sample | Conc. μg/mL | IL-1β (pg/mL) | % reduction in IL-1 β levels |
|---|---|---|---|
| LPS Control | 0.1 | 146.89 | 0.00 |
| Cucumber | 25 | 136.21 | 7.27 |
| extract Batch | 50 | 130.96 | 10.84 |
| B17CF007 | 100 | 121.89 | 17.02 |
|  | 200 | 113.80 | 22.53 |

There was an increase in the anti-inflammatory marker IL-10 both with idoBR1 & cucumber extracts 3.04 & 3.65 fold respectively. The IL-10 results indicate anti-inflammatory effects. IdoBR1 at 100 μg/mL exhibited 24.53% reduction of IL-12 levels in the LPS-induced inflammatory response in THP-1 cells as compared to the LPS control. Cucumber extract Q-actin at 200 μg/mL showed a 25.88% reduction of IL-12 levels in the LPS-induced inflammatory response in THP-1 cells as compared to the LPS control. IdoBR1 at 100 μg/mL gave a 24.07% reduction of IL-1β levels in the LPS-induced inflammatory response in THP-1 cells as compared to the LPS control. Cucumber extract Q-actin at 200 μg/mL showed the highest reduction of IL-1β levels (22.53%) in the LPS-induced inflammatory response in the THP-1 cells.

Example 6: Gym Workout with Q-Actin Increases IL-10 Measured in Human Blood

Introduction

We have shown modulation of the anti-inflammatory cytokine IL-10 in THP-1 cells by idoBR1 and cucumber extract (Q-actin). The modulation of the cytokine in people taking Q-actin and given intense exercise regimes that naturally causes muscle inflammatory responses is tested here.

Method

In an exercise recovery experiment, using 7 placebo subjects and 10 Q-actin subjects, IL-10 was measured in blood samples. The subjects were given either 10 mg of Q-actin twice a day or a placebo (both in capsules) from day 0 for 4 days with intensive exercise on days 1, 2, 3 and day 4 (being a recovery day). Blood samples were taken before and after exercise on days 1, 2, 3 and at the end of recovery day 4. IL-10 was measured by ELISA assays.

Results

The subjects given Q-actin showed a trend towards a significantly greater increase in IL-10 once exercise had started and confirming the results obtained in LPS-stimulated THP-1 cells.

Table Showing the IL-10 Response of Blood from Subjects Given an Intense Exercise Routine (Plus and Minus Q-Actin, Cucumber Extract with >1% idoBR1)

| | | base | D1-pre | D1-1H | D2-pre | D2-1H | D3-pre | D3-1H | D4-pre |
|---|---|---|---|---|---|---|---|---|---|
| placebo | Mean | 51.84 | 62.05 | 77.92 | 63.49 | 72.03 | 59.65 | 68.03 | 58.82 |
| | SD | 15.65 | 4.66 | 12.55 | 8.81 | 6.42 | 6.58 | 12.63 | 6.25 |
| | SEM | 5.92 | 1.76 | 4.74 | 3.33 | 2.43 | 2.49 | 4.77 | 2.36 |
| Q-actin | Mean | 64.22 | 60.12 | 92.45 | 64.36 | 88.30 | 54.96 | 85.79 | 55.90 |
| | SD | 16.82 | 19.54 | 31.63 | 23.87 | 34.64 | 25.00 | 35.91 | 23.59 |
| | SEM | 5.95 | 6.91 | 11.18 | 8.44 | 12.25 | 8.84 | 12.69 | 8.34 |

D1-pre = blood sampled before exercise
D1-1H = blood sampled 1 hour after exercise

Example 7: MAPK Signalling Effects of idoBR1 and Cucumber Extract Containing idoBR1

Introduction

MAPK signaling cascade plays an essential role in the initiation of inflammatory responses. The induction of inflammatory cytokine genes requires activation of the MAPKs and stimulation of extracellular regulated protein kinases/mitogen-activated protein kinase (ERK/MAPK) pathways are essential for downstream inflammatory responses (Kaminska, B., 2005, Biochim. Biophys. Acta, 1754, 253; Buchholz, K. et al., 2007, Infection and Immunity, 75, 5924). The MAPK pathway is also required for the expression of inflammatory mediator genes, including COX-2, iNOS, IL-1β, and TNF-α. It was reported that ERK and/or p38 MAPK are involved in up-regulation of IL-1β (Baldassare, J. et al., 1999. J. Immunol., 162, 5367).

Method

THP-1 cells were cultured in RPMI media supplemented with mercaptoethanol & glutamine to get 80% confluence in culture flasks, then they were aspirated and centrifuged at 1500 rpm for 5 mins. The cell pellet was then resuspended in 1 ml of RPMI complete media and counted conventionally using a hemocytometer. The cells (5×106) were incubated with PMA (10 ng/ml) in separate dishes to differentiate THP-1 cells. To determine the protein expression p38 & p42/44, THP-1 cells were pre-treated for 1 hr with idoBR1-100 μg/ml & 50 μg/ml and cucumber extract (Q-actin batch no. B17CF001)—200 μg/ml & 100 μg/ml, followed by 2 hr LPS (1 μg/ml) stimulation. Post incubation, the cells were harvested and whole protein was isolated.

Western Blot Procedure

Cell pellets were lysed, and the protein concentration was determined using the Bio-Rad protein determination assay (Bio-Rad). Total cell proteins were subjected to 8% polyacrylamide SDS gel electrophoresis followed by transfer onto polyvinylidene difluoride membranes (Thermoscientific). The membranes were probed with either mouse anti-phospho-p38 mAb (Thermoscientific) or mouse anti-phospho-p42/44 mAb (Thermoscientific), followed by horseradish peroxidase-conjugated goat anti-mouse polyclonal antibodies (Thermoscientific). All immunoblots were visualized by ECL (Amersham Biosciences). The test samples Q-Actin tested at 100 μg/ml & 200 μg/ml showed relative reduction in phosphorylated p38 expression of 0.92 and 0.83 respectively compared to the LPS control. In case of idoBR1 at 50 μg/ml & 100 μg/ml it showed reduction in phosphorylated p38 expression of 0.88 and 0.80 respectively compared to the LPS control. Q-actin tested at 100 μg/ml & 200 μg/ml showed relative reduction in phosphorylated ERK 42/44 expression of 0.81 and 0.78 respectively compared to LPS control. IdoBR1 at 50 μg/ml & 100 μg/ml showed reduction in phosphorylated ERK 42/44 expression of 0.80 and 0.76 respectively compared to the LPS control.

Table Showing Relative Expression of p42/44

| Test samples | Conc, (μg/ml) | Relative expression |
|---|---|---|
| LPS | 1 | 1.00 |
| Q-actin | 100 | 0.81 |
| Q-actin | 200 | 0.78 |
| idoBR1 | 50 | 0.80 |
| idoBR1 | 100 | 0.76 |

Table Showing Relative Expression of p38.

| Test samples | Conc, (μg/ml) | Relative expression |
|---|---|---|
| LPS | 1 | 1.00 |
| Q-actin | 100 | 0.92 |
| Q-actin | 200 | 0.83 |
| idoBR1 | 50 | 0.88 |
| idoBR1 | 100 | 0.80 |

Both idoBR1 and cucumber extract containing idoBR1 (Q-actin) are therefore shown to be able to reduce the MAPK signaling cascade that plays an essential role in the inflammatory response.

Example 8: Oral Availability and In Vivo Stability of idoBR1

Introduction

The purpose of this study was to investigate the oral availability of idoBR1 from eaten cucumber/gherkin by measuring it in urine. This study indicated not only oral availability and possible systemic activity of idoBR1 but also supported the ability of the compound to pass through membranes unaltered and, therefore, also support topical availability.

Method

Parisien pickling cucumbers (seeds purchased from Lidl 2013) were grown organically and three eaten at midday by each of one male volunteer and one female volunteer. The fresh weight consumed was 260 g in each case with a comparable weight of 30 g removed from all the cucumbers consumed and this was kept for analysis. The volunteers ate no Cucurbitaceae food for 15 hours prior to the experiment. Urine samples pre-consumption were collected over 3 hours as t=0 and then samples collected for 9 hours for the female and 15 hours for the male. The 30 g cucumber sample was homogenised in 50% ethanol (aq) and after 15 hours extraction it was filtered and the idoBR1 fraction bound to cation exchange resin IR120 in the H+ form. After washing the column with water, the material displaced with 2M ammonia solution was dried (52.3 mg) and analysed by GC-MS after trimethylsilylation using Pierce TriSil. The remaining 51 mg of material then had 0.2 mg of castanospermine added for comparative quantification purposes. The entire urine samples were similarly treated using cation exchange resin except the material displaced by ammonia solution was run a second time through the same cation exchange resin (now in the ammonium form) to reduce strong bases (which will bind to IR120 in the ammonium form) and only the unretained material was kept. The urine idoBR1 fractions were dried and made up to 20 ml in water. 500 ul of each was sampled and 0.025 mg of castanospermine added.

Results

GCMS Analysis of Cucumber

This was carried out on a Perkin Elmer Turbomass Gold GCMS. The spectrum of the major peak at 10.33 mins matched the GCMS spectrum of authentic idoBR1, 900288 PhytoQuest Ltd, UK). The relative response factor was calculated between authentic BR1 (900125, PhytoQuest Ltd) and castanospermine is 1:2. Assuming the same response factor, the amount of idoBR1 was estimated as 1.5 mg in the 30 g sample which means that the volunteers consumed roughly 260/30×1 5 mg=13 mg of idoBR1.

Urine Results

The urine samples collected before consumption of the cucumbers showed no significant peaks at the retention time of idoBR1 (10.33 min). After 15 hours the male showed excretion of approximately 2.4 mg of idoBR1 compared to the castanospermine reference peak area but more accurate measurement of intake and excretion would be required for definitive mass balance. The female had excreted approximately 2.1 mg of idoBR1. This study confirmed idoBR1 was available orally and it could be measured in urine which means it can enter the blood stream from oral ingestion and, at least a significant proportion, is excreted unchanged in urine. This shows that the compound can pass through membranes in the digestive tract and is significant in urine. No obvious conjugation was observed in the urine analysis.

It is possible that the remaining idoBR1 remained in the body for longer. Thus, it appears that it may be a potent anti-inflammatory agent and that it may be long-lasting.

Example 9: Effect of idoBR1 on Microglial Cells

Introduction

Microglial cells are the resident macrophages of the central nervous system (CNS). These cells are a primary form of active immune defense in the CNS. In neurodegenerative disorders such as Alzheimer's and Parkinson's disease, microglia are chronically activated and promote the release of pro-inflammatory cytokines which further disrupt normal CNS activity. There is considerable interest in examining the extent to which bioactive food components can mitigate the effects of inflammation by decreasing oxidative stress and/or by decreasing pro-inflammatory gene expression.

Method idoBR1 was used in cell cultures of murine microglial cell line BV-2 at 0, 20, 40 and 80 μg/ml plus and minus sub-optimal LPS. Production of TNF-α and nitrite was measured after 24 hours. Interestingly, idoBR1 from Q-actin was found to be effective at reducing TNF-α and nitrite production by the stimulated microglial cells.

| idoBR1 μg/ml | No LPS | 0 | 20 | 40 | 80 |
|---|---|---|---|---|---|
| Nitrite production μM | 3 | 14*** | 11* | 9** | 8** |
| TNF-α production pg/ml | 50 | 600*** | 500** | 470** | 410*** |

*significance calculated plus/minus LPS and for test samples against LPS plus 0 idoBR1 (n => 3)
Cells were pre-treated with compound 30 minutes prior to stimulation with LPS for a further 24 hours. Data of all experiments are represented as a mean ± SEM of at least 3 experiments. Values were compared using one-way ANOVA followed by a post-hoc Student Newman-Keuls test. Data were analysed using the GraphPad Prism software.
*p < 0.05;
**p < 0.01;
***p < 0.001

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of treatment or prophylaxis for a disease or disorder, the method comprising administering an effective amount of idoBR1 to a subject in need thereof,
   wherein the disease or disorder is a viral infection or bacterial infection mediated by sialidase activity.

2. The method of claim 1, wherein the method comprises inhibiting commensal and/or pathogenic bacterial growth in vivo.

3. The method of claim 2, wherein the method comprises disrupting host-bacterial cell interactions, and/or inhibiting or eliminating bacterial biofilm formation in the subject.

4. The method of claim 1, wherein the subject is a mammalian subject.

5. The method of claim 4, wherein the mammalian subject is a human subject.

6. The method of claim 1, wherein the disease or disorder is mediated or characterized by the presence of bacterial biofilms.

7. The method of claim 6, wherein the biofilms are selected from sub-gingival plaque biofilms and mucosal biofilms.

8. The method of claim 7, wherein the disease or disorder is periodontal disease, bacterial vaginosis and/or diseases caused by infection with *Tannerella forsythia, Tannerella denticola, Porphyromonas gingivalis* or *Gardnerella vaginalis*.

9. A method of modulating commensal bacterial growth in a mammalian host, the method comprising administering a sialidase inhibitory amount of idoBR1 to the mammalian host.

10. The method of claim 9, wherein the composition of commensal bacteria in the mammalian host is modulated.

11. The method of claim 9, wherein the mammalian host is a human host.

* * * * *